United States Patent [19]
Johnson

[11] Patent Number: 5,782,924
[45] Date of Patent: Jul. 21, 1998

[54] FIXATION METHOD AND APPARATUS FOR TOTAL JOINT PROSTHESIS

[76] Inventor: Lanny L. Johnson, 2950 E. Mount Hope Rd., Okemos, Mich. 48864

[21] Appl. No.: 694,467

[22] Filed: Aug. 8, 1996

[51] Int. Cl.⁶ .................................................. A61F 2/38
[52] U.S. Cl. .................................. 623/20; 623/18
[58] Field of Search ........................ 623/20, 16, 18

[56] References Cited

U.S. PATENT DOCUMENTS

| | | | |
|---|---|---|---|
| 4,919,671 | 4/1990 | Karpf | 623/20 |
| 5,092,895 | 3/1992 | Albrektsson | 623/20 |
| 5,137,536 | 8/1992 | Koshino | 623/20 |
| 5,425,777 | 6/1995 | Sarkisian | 623/20 |
| 5,549,684 | 8/1996 | Amino | 623/20 |
| 5,571,196 | 11/1996 | Stein | 623/20 |
| 5,645,602 | 7/1997 | Albrektsson | 623/20 |

FOREIGN PATENT DOCUMENTS

| | | | |
|---|---|---|---|
| 2630640 | 11/1989 | France | 623/20 |
| 719625 | 3/1980 | U.S.S.R. | 623/20 |

*Primary Examiner*—Michael J. Milano
*Attorney, Agent, or Firm*—Cushman Darby & Cushman IP Group of Pillsbury Madison & Sutro LLP

[57] ABSTRACT

A bone surface is initially shaped to conform with a surface of an artificial joint prosthesis. At least one leg projects from said surface of the prosthesis, the leg having a major axis extending substantially parallel said surface and being tapered so as to snugly fit within a substantially corresponding configured channel formed in the bone adjacent its shaped surface.

1 Claim, 1 Drawing Sheet

FIXATION METHOD AND APPARATUS FOR TOTAL JOINT PROSTHESIS

BACKGROUND OF THE INVENTION

1. Field of the Invention

The present invention relates to improved fixation for artificial joint implants.

2. The Prior Art

There are various anatomical regions suitable for accommodating a joint prosthesis. These include, for example, shoulders, hips and knees. Conventional means for affixing the prosthesis to a joint typically employ screws and/or cements to fasten the prosthesis to the prepared site. Alternatively, in certain applications the prosthesis is provided with a mesh, beaded or cindered surface which is forced against bleeding bone with the objective that fibrous bone ingrowth occur to bind the bone to the aforesaid surface of the prosthesis.

Previously employed fixation arrangements have proven to be unreliable. The introduction of screws to the bone often results in stress risers that weaken fixation, and the use of screws can provide conduits for synovial fluid and wear particles which can cause bone to dissolve thereby loosening the prosthesis.

SUMMARY OF THE INVENTION

The present invention eliminates reliance on screws, cement and bone growth as the primary means for securing a prosthesis to bone. Instead, once the bone surface to which the prosthesis is to be fixed is prepared, at least one channel is formed in the bone extending across the prepared surface. The channel is tapered from one end to the other, and its principal cross-section underlies the prepared surface such that only a slot-like communication exists between the interior of the channel and the exterior side of the prepared surface. The surface of the prosthesis intended to mate with the prepared bone surface is provided with at least one appended leg which is configured to substantially correspond with the tapered channel in the bone. The narrow end of the leg is introduced to the wide end of the channel which opens to one side of the bone to which the prosthesis is to be secured. The prosthesis then is inserted into the channel until the leg is fully received within the channel. At such position, the prepared surface overlies a portion of the leg thereby retaining the prosthesis at a fixed location. By dimensioning the channel slightly smaller than the tapered leg, a force fit is achieved between the two whereby resistance to withdrawal of the leg from the channel is achieved.

BRIEF DESCRIPTION OF THE DRAWINGS

The invention now will be described in further detail by reference to the accompanying drawings wherein.

DETAILED DESCRIPTION OF PREFERRED EMBODIMENTS OF THE INVENTION

The following description of the invention relates to the implantation of a prosthesis in shoulder surgery. However, the invention is equally applicable to other procedures, including knee and hip surgery.

Figure 1:
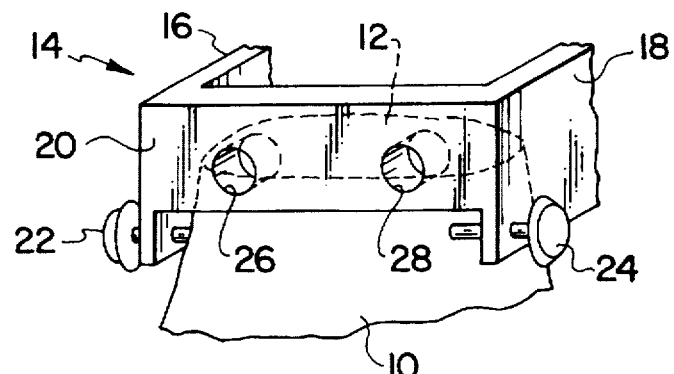
FIG. 1 is a fragmented perspective view of a device for forming channels in bone in preparation for the attachment of a prosthesis to the bone.

Referring to FIG. 1, a segment of a glenoid is illustrated which is generally identified as 10. In preparation for the surgery, the end of the glenoid is exposed and is flattened to a plane surface 12 by conventional cutting devices. A jig 14 is secured to the flattened end of the glenoid. The jig is a box-like device which includes opposed sidewalls 16 and 18 and opposed endwalls 20, only one of which is illustrated. The jig is open at its top and bottom so that it may be slipped over the free end of the glenoid. The opposed sidewalls carry respective clamping screws 22 and 24 which are adjustable so as to secure the jig to the glenoid at any desired location. At least one of the endwalls 20 is provided with apertures 26 and 28 which are oriented relative to one another so that the jig can be selectively clamped to locate the apertures proximate the flattened of surface 12 of the glenoid. More particularly, the apertures 26 and 28 are positioned relative to surface 12 such that a plane which includes the longitudinal axes of the apertures lies below the plane of surface 12.

Figure 2:
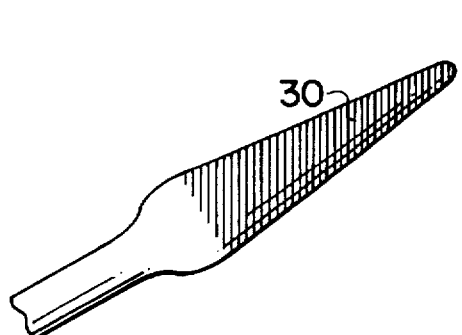
FIG. 2 is an elevational view of a drill bit used when forming channels in bone with the device shown in FIG. 1.
Figure 3:
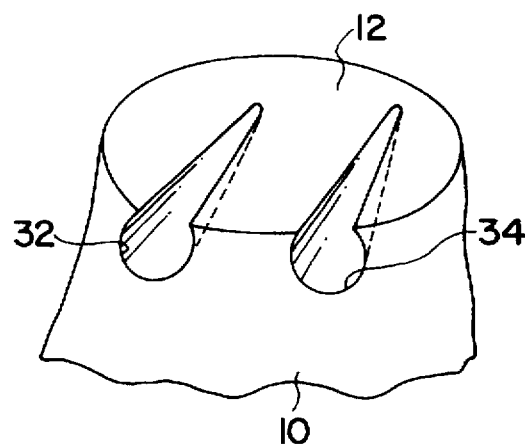
FIG. 3 is a perspective view of a segment of bone in which a pair of channels are formed utilizing the apparatus shown in FIGS. 1 and 2.

When the jig 10 is clamped relative to surface 12 as just described, a drill bit is introduced into apertures 26 and 28. An appropriate drill bit 30 is illustrated in FIG. 2. The bit is tapered and is provided with cutting edges arranged to cut bone and to compress the debris created by the cutting operation against the wall of the bore which is formed in the bone during drilling. Thus, when the drill bit passes through apertures 26 and 28 to engage the glenoid, the surface 12 is cut away beginning on one side of the glenoid, and channels 32 and 34 (FIG. 3) are formed in the glenoid which extend along axes which are substantially transverse to the longitudinal axis of the glenoid. The channels are generally oriented in spaced parallel relationship.

Because of the longitudinal axes of apertures 26 and 28 being fixed at a level below that of surface 12, substantially parallel slots are formed in surface 12 whereby the channels 32 and 34 communicate with the exterior side of surface 12. However, the widths of the slots are less than the maximum widths of the channels. Thus, the edges of the slots overlie the channels. This permits a prosthesis to be secured to the glenoid, as now will be described.

Figure 4:
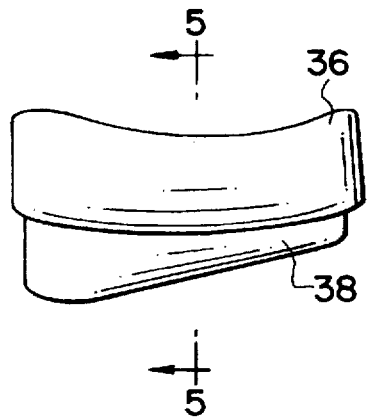
FIG. 4 is an elevational view of a prosthesis suitable for attachment to the segment of bone shown in FIG. 3.
Figure 5:
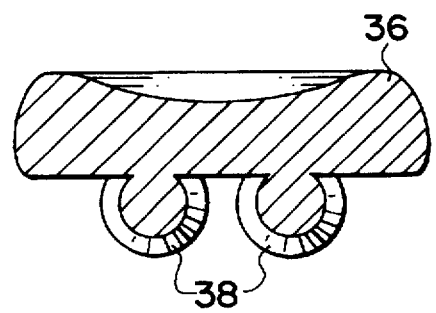
FIG. 5 is a sectional view taken along line 5—5 of FIG. 4.

Referring to FIGS. 4 and 5, a prosthesis suitable for use in an artificial shoulder joint is generally identified as 36. This prosthesis can be formed of metal and/or plastic in a conventional manner. The prosthesis includes a pair of spaced, substantially parallel projecting legs 38 on one side thereof. The legs 38 are configured to generally correspond to the shape of the channels 32 and 34 formed in glenoid 10. Preferably, however, the cross-sectional widths of legs 38 are slightly greater than the corresponding dimensions of the channels so that when the legs 38 are inserted into the channels, a snug fit will be achieved which will resist withdrawal of the prosthesis from the bone.

To join the prosthesis 36 to the glenoid 10, the narrow ends of legs 38 are inserted into the larger openings of channels 32 and 34 on the side of the glenoid. The prosthesis is slid laterally, in a direction substantially transverse to the glenoid's longitudinal axis, to advance the legs 38 within the respective channels 32 and 34. Because the legs preferably are slightly wider than the channels, insertion is completed by tapping the prosthesis into its final position. When so located, the major cross-sectional dimensions of the legs 38 underlie the narrower slots formed by the channels in surface 12 of the glenoid. This prevents the prosthesis from being pulled from the glenoid in the direction of the glenoid's longitudinal axis. Also, by virtue of the legs 38 and being snugly seated within elongated channels 32 and 34, the attachment of the prosthesis to the glenoid is strongly resistant to rotational forces tending to displace the prosthesis relative to the glenoid.

By the arrangement which has been described, the deficiencies of screws, cements and ingrowth of bone as the primary means for securing a prosthesis to bone are overcome. Of course, the improvement in fixation achieved by the present invention in some instances can be enhanced by selectively using screws, cements and/or bone ingrowth as secondary fastening means.

The arrangement described additionally resists compression and angulation forces because the means for securing the prosthesis to bone is spread across a wide area underlying those areas where such forces normally are encountered.

Although the arrangement disclosed employs two legs 38 to secure the prosthesis, it is possible in some instances to utilize a single leg received in a single channel in the bone. Of course, it also is possible to provide more than two legs with a corresponding number of channels.

In describing the invention with respect to the shoulder joint, the glenoid was prepared by planing a flat surface 12 prior to forming the channels. For a joint such as the hip, the concave shape of the acetabulum would require a different type of jig so as to form channels in a curved surface. However, the principles described above with respect to a shoulder prosthesis would still apply in that the hip prosthesis would include one or more tapered legs on its concave surface which would be inserted into a respective channel(s) in the acetabulum.

What is claimed is:

1. An artificial joint prosthesis adapted to be secured to a surface of a bone, said prosthesis comprising:

a body portion having a surface configured to substantially conform with the surface of the bone to which the prosthesis is to be secured;

a plurality of spaced legs projecting from said body portion surface, said legs having major axes substantially parallel to one another and extending substantially parallel to said body portion surface, said legs additionally being tapered in the direction of their respective axis over substantially the entire length of the legs, said tapered legs being configured in cross-section as circular segments having arcs greater than semicircular and chords located at said body portion surface.

* * * * *